(12) United States Patent
van der Bruggen et al.

(10) Patent No.: US 6,328,971 B1
(45) Date of Patent: *Dec. 11, 2001

(54) MAGE-1 DERIVED NONA PEPTIDES, AND COMPOSITIONS THEREOF

(75) Inventors: Pierre van der Bruggen; Thierry Boon-Falleur, both of Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/292,492

(22) Filed: Aug. 18, 1994

Related U.S. Application Data

(63) Continuation-in-part of application No. 08/195,186, filed on Feb. 14, 1994, now Pat. No. 5,558,995, which is a continuation-in-part of application No. 08/196,630, filed on Feb. 15, 1994, now Pat. No. 5,683,886, which is a continuation-in-part of application No. 08/008,446, filed on Jan. 22, 1993, now abandoned.

(51) Int. Cl.[7] .................. A61K 38/03; A61K 39/385; A61K 47/00; C07K 17/00
(52) U.S. Cl. .................... 424/185.1; 424/193.1; 424/278.1; 530/328
(58) Field of Search .................. 530/300, 326–9, 530/328; 536/23; 424/185.1, 193.1, 278.1

(56) References Cited

U.S. PATENT DOCUMENTS

| | | | |
|---|---|---|---|
| 5,066,783 | * | 11/1991 | Cohen et al. . |
| 5,558,995 | * | 9/1996 | van der Bruggen . |
| 5,683,886 | * | 11/1997 | van der Bruggen . |
| 6,037,135 | * | 3/2000 | Kubo et al. . |
| 6,110,694 | * | 8/2000 | Boel et al. . |

FOREIGN PATENT DOCUMENTS

92/13069 * 8/1992 (WO) .

OTHER PUBLICATIONS

Aichele, P. et al., J. Exp. MEd. 171:1815–1820, "Antiviral cytotoxic T cell response induced by in vivo priming with a free synthetic peptide", May 1990.*

Engelhard, V. H. et al., Curr. Opin. Immunol. 6:13–23, "Structure of peptides associated with MHC Class I molecules", 1994.*

Mogard, M. H. et al., Biochem. Biophys. Res. Comm. 136:983–988, "The amino acid sequence of kinetensin, a novel peptide isoalted from pepsin–treated plasma: homology with human serum albumin, neurotensin and angiotensin", May 14, 1986.*

Palfreyman, J. W. et al., J. Immunol. Meth. 75:383–393, "Guidelines for the production of polypeptide specific antisera using small sythetic oligopeptides as immunogens", 1984.*

Parker, K.C. et al., J. Immunol. 149:3583–3587, "Sequence motifs important for peptide binding to the human MHC Class I molecule, HLA–A2", 1992.*

Salgaller, M. L. et al., Cancer Immunol. Immunother. 39:105–116, "Generation of specific anti–melanoma reactivity by stimulatin of human tumor–infiltrating lymphocytes with MAGE–1 synthetic peptide", 1994.*

Smilek, D. et al., PNAS 88:9633–9637, A single amino acid change in a myelin basic protein peptide confers the capacity to prevent rather than induce experimental autoimmune encephalomyelitis, Nov. 1991.*

Walter, G., et al., PNAS 78:4882–4886, "Antibodies specific for the polyoma virus middle–sized tumor antigen", Aug. 1981.*

Young, C. R. et al., Mol. Immunol. 20:567–570, Antibodies with specificities to preselected protein regions evoked by free synthetic peptides, 1983.*

* cited by examiner

Primary Examiner—Christina Chan
Assistant Examiner—Marianne DiBrinno
(74) Attorney, Agent, or Firm—Fulbright & Jaworski, LLP

(57) ABSTRACT

This invention relates to MAGE-1 derived nonapeptides. The therapeutic and diagnostic ramifications of this observation are the subject of the invention.

4 Claims, 2 Drawing Sheets

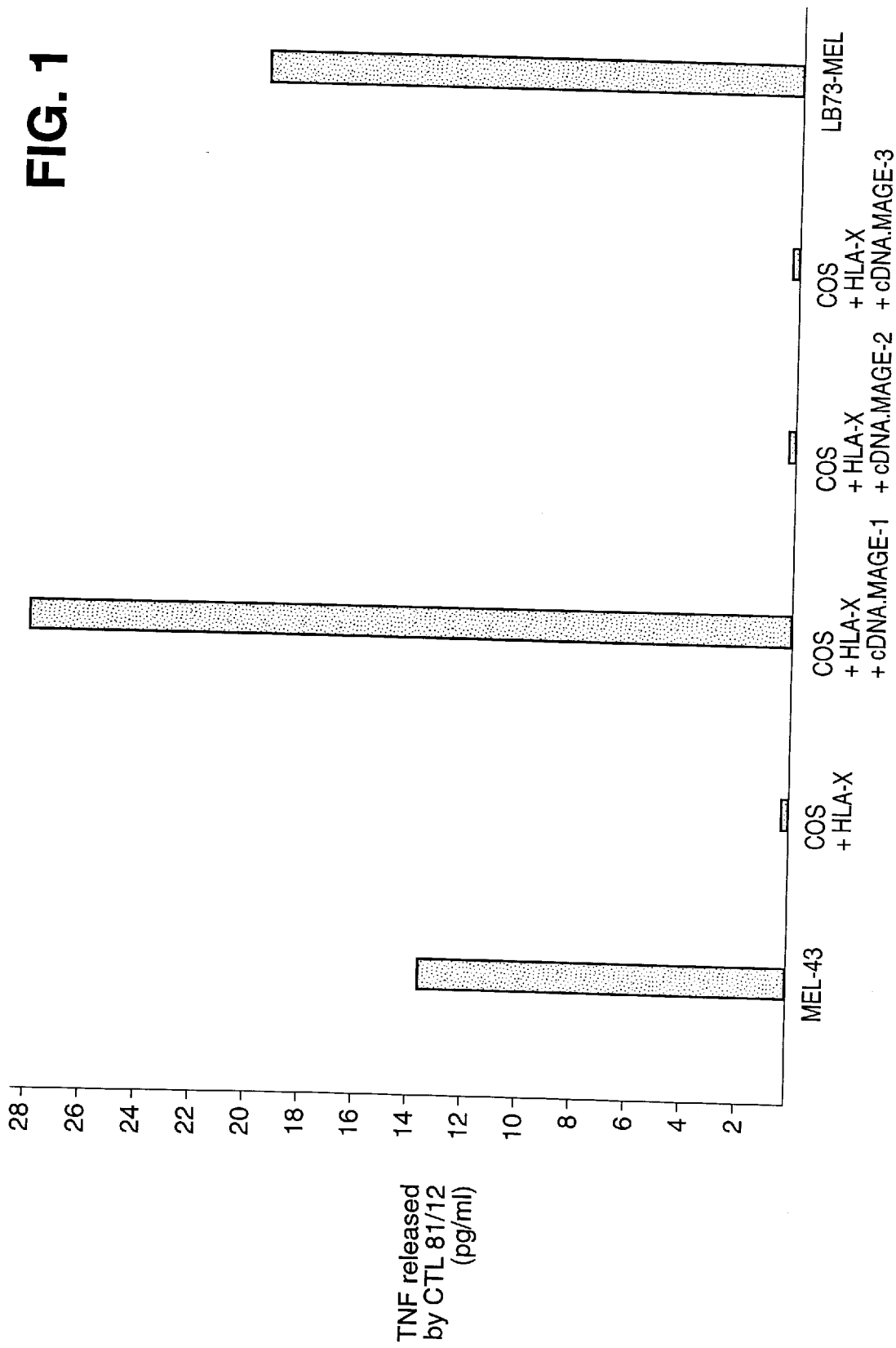

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 1:

ACTCCATGAG GTATTTC                                              17

(2) INFORMATION FOR SEQ ID NO: 2:

(i) SEQUENCE CHARACTERISTICS:
      (A) LENGTH: 16 amino acid residues
      (B) TYPE: amino acid
      (D) TOPOLOGY: linear (xi) SEQUENCE DESCRIPTION: SEQ ID NO: 2:

Glu His Ser Ala Tyr Gly Glu Pro Arg Lys Leu Leu Thr Gln Asp Leu
                 5                         10                15

(2) INFORMATION FOR SEQ ID NO: 3:

(i) SEQUENCE CHARACTERISTICS:
      (A) LENGTH: 12 amino acid residues
      (B) TYPE: amino acid
      (D) TOPOLOGY: linear (xi) SEQUENCE DESCRIPTION: SEQ ID NO: 3:

Glu His Ser Ala Tyr Gly Glu Pro Arg Lys Leu Leu
                 5                         10

(2) INFORMATION FOR SEQ ID NO: 4:

(i) SEQUENCE CHARACTERISTICS:
      (A) LENGTH: 9 amino acid residues
      (B) TYPE: amino acid
      (D) TOPOLOGY: linear (xi) SEQUENCE DESCRIPTION: SEQ ID NO: 4:

Ser Ala Tyr Gly Glu Pro Arg Lys Leu (2) INFORMATION FOR SEQ ID NO: 5:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 5:

Ala Ala Arg Ala Val Phe Leu Ala Leu
               5

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 6:

CAAGCGCCAG GCACAGA                                           17

(2) INFORMATION FOR SEQ ID NO: 7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 7:

GCCTCATGGT CAGAGACGA                                    19

(2) INFORMATION FOR SEQ ID NO: 8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 8:

GAGTGAGCCT GCGGAAC                                           17

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 9:

CCTCCAGGTA GGCTCTCT                                        18

(2) INFORMATION FOR SEQ ID NO: 10:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 10:

Xaa Ala Xaa Xaa Xaa Xaa Xaa Xaa Leu
               5

(2) INFORMATION FOR SEQ ID NO: 11

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 11:

Ser Ala Tyr Xaa Xaa Xaa Xaa Xaa Leu
              5

(2) INFORMATION FOR SEQ ID NO: 12:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 12:

Xaa Ala Tyr Gly Xaa Xaa Xaa Xaa Leu
              5

(2) INFORMATION FOR SEQ ID NO: 13:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 13:

Xaa Ala Tyr Xaa Glu Xaa Xaa Xaa Leu
              5

(2) INFORMATION FOR SEQ ID NO: 14:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 14:

Xaa Ala Tyr Xaa Xaa Pro Xaa Xaa Leu
              5

(2) INFORMATION FOR SEQ ID NO: 15:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 15:

Xaa Ala Tyr Xaa Xaa Xaa Arg Xaa Leu
              5

(2) INFORMATION FOR SEQ ID NO: 16:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 16:

Xaa Ala Tyr Xaa Xaa Xaa Xaa Lys Leu
              5

```
(2) INFORMATION FOR SEQ ID NO: 17:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 17:

Xaa Ala Tyr Xaa Xaa Xaa Xaa Xaa Leu
```

MAGE-1 DERIVED NONA PEPTIDES, AND COMPOSITIONS THEREOF

RELATED APPLICATIONS

This application is a continuation-in-part of application Ser. No. 08/195,186 filed Feb. 14, 1994 now U.S. Pat. No. 5,558,995, which is a continuation-in-part of U.S. application Ser. No. 08/008,446, filed Jan. 22, 1993 now abandoned. It is also a continuation-in-part of Ser. No. 08/196,630 filed Feb. 15, 1994 now U.S. Pat. No. 5,683,386.

FIELD OF THE INVENTION

This invention relates to various therapeutic methodologies derived from the recognition that certain abnormal cells present complexes of HLA-Cw*1601 (previously referred to as HLA-C-clone 10) (Bodmer et al., Tissue Antigens 44: 1 (1994)) and peptides derived from a molecule referred to as MAGE-1 on their surfaces. In addition, it relates to the ability to identify those individuals diagnosed with conditions characterized by cellular abnormalities whose abnormal cells present this complex.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J.P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, as WO92/20356 and incorporated by reference, a family of genes is disclosed which are processed into peptides which, in turn, are expressed on cell surfaces, and can lead to lysis of the tumor cells by specific CTLs. These genes are referred to as the "MAGE" family, and are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes.

In U.S. patent application Ser. No. 938,334, the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In a patent application filed on Dec. 22, 1992 in the name of Boon-Falleur et al., entitled "Method For Identifying Individuals Suffering From a Cellular Abnormality, Some of Whose Abnormal Cells Present Complexes of HLA-A2/Tyrosinase Derived Peptides and Methods for Treating said Individuals", the complex of the title was identified as being implicated in certain cellular abnormalities. The application does not suggest, however, that any other HLA molecules might be involved in cellular abnormalities.

The prior presentation of MAGE-1 by an HLA-A molecule, as disclosed supra, also does not suggest that the protein can be presented by another HLA molecule. Thus, it is surprising that the very MAGE molecule presented by HLA-A1 has now been shown to be presented by HLA-Cw*1601. While the prior research is of value in understanding the phenomenon, it in no way prepares the skilled artisan for the disclosure which follows.

BRIEF DESCRIPTION OF THE FIGURE

FIG. 1 depicts experiments involving transfection of COS-7 with coding sequences for MAGE-1 and HLA-Cw*1601.

DETAILED DESCRIPTION OF PREFERRED EMBODIMENTS

EXAMPLE 1

Figure 2A:
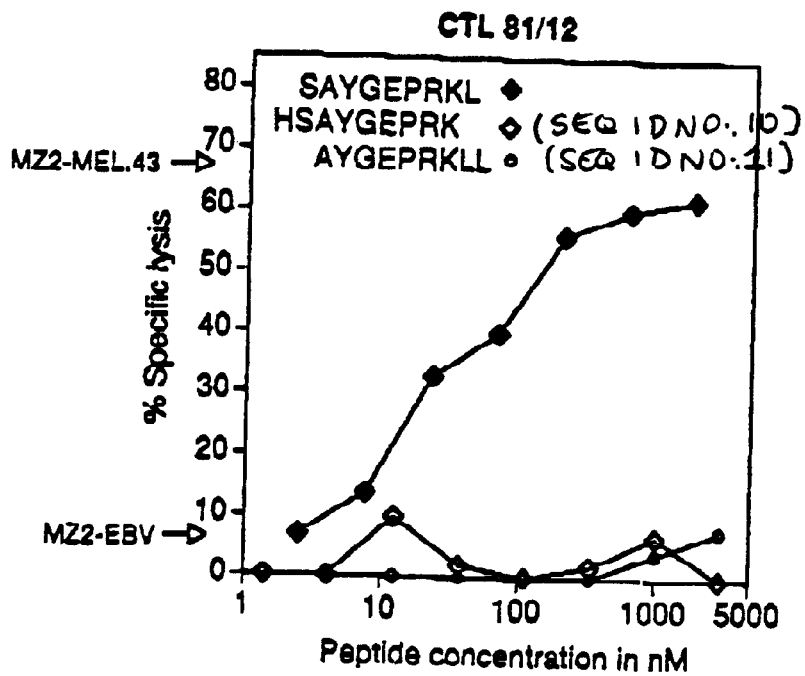
FIG. 2A sets forth results of a $^{51}$Cr release assay using MZ2 cells infected with Epstein Barr Virus, which had been incubated with the peptide of SEQ ID NO: 4, for 30 minutes. The effector cells were from CTL 81/12.

In the experiments which follow, various melanoma cell lines were used. These were obtained from melanoma patients identified as MZ2 and LB73. Cell lines MZ2-MEL.43, MZ2-MEL-3.0, and MZ2-MEL3.1 are cloned sublines of MZ2-MEL, and are described in Van den Eynde et al., Int. J. Canc. 44: 634 (1989), as well as PCT patent application WO92/20356 (Nov. 26, 1992), both disclosures being incorporated by reference and in their entirety herewith. Cell line LB73-MEL was derived from patient LB73 in the same manner as the other cell lines described herein.

Samples containing mononuclear blood cells were taken from patient MZ2. A sample of the melanoma cell line MZ2-MEL.43 was irradiated, and then contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 μCi/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% of CO$_2$ atmosphere.

Plates were centrifuged again, and 100 ul aliquots of supernatant were collected and counted. Percentage of $^{51}$Cr release was calculated as follows:

$$\% \ ^{51}Cr \ release = \frac{(ER-SR)}{(MR-SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

These experiments led to the isolation of several CTL clones from patient MZ2 including CTL clone "81/12".

The experiment was repeated as described, using both cell line MZ2-MEL 3.0 and MZ2-MEL 3.1. The results indicated that clone 81/12 recognized both MZ2-MEL.43 and MZ2-MEL 3.0, but not MZ2-MEL 3.1. The antigen being recognized by 81/12 is referred to hereafter as "antigen Bb".

EXAMPLE 2

In view of prior work, as summarized supra, it was of interest to determine the HLA class 1 profile for patient MZ2. This was determined following standard methodologies, which are now set forth. To obtain cDNA clones coding for the genes of the HLA class 1 molecules of the patients, a cDNA library was prepared, starting with total mRNA extracted from cell line MZ2-MEL.43, using well known techniques not repeated here. The library was inserted into plasmid pcD-SRα, and then screened, using an oligonucleotide probe containing a sequence common to all HLA class 1 genes, i.e.:

5'-ACTCCATGAGGTATTTC-3' (SEQ ID NO: 1)

One clone so identified was clone IC4A7 which, upon sequencing, was found to be functionally equivalent, if not identical to, HLA-Cw*1601, a well known human leukocyte antigen molecule. The sequence of the DNA coding for HLA-Cw*1601 is given at, e.g. Cianetti et al., Immunogenetics 29: 80–91 (1989), where it was named HLA-C clone 10 and the sequence is available under GENBANK accession number HUMMHCACA. An updated sequence is reported by Zemmour et al., Immunogenetics 37: 239–250 (1993), the disclosure of which is incorporated by reference in its entirety, as is Cianetti et al., supra. The Zemmour sequence is also available in the EMBL sequence bank.

EXAMPLE 3

It was of interest to determine if the HLA molecule identified supra presented a mage derived tumor rejection antigen, and if the resulting complex of antigen and HLA molecule was recognized by a CTL clone of patient MZ2. To determine this, recipient cells were transfected with cDNA coding HLA-Cw*1601, and with one of MAGE-1, MAGE-2, or MAGE-3 cDNA. The MAGE-1 cDNA was inserted into plasmid pcDNA I/Amp, while MAGE-2 and MAGE-3 cDNA were inserted into plasmid pcD-SRα.

Samples of recipient COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, and 100 ng of the subject plasmids (i.e., 100 ng of the IC4A7 clone, and 100 ng of the MAGE-cDNA plasmid). Following four hours of incubation at 37° C., the medium was removed, and replaced by 50 μl of PBS containing 10% DMSO. This medium was removed after two minutes and replaced by 200 μl of DMEM supplemented with 10% FCS.

Following this change in medium, COS cells were incubated for 48 hours at 37° C. Medium was then discarded, and 2000 cells of CTL clone 81/12 were added, in 100 μl of Iscove medium containing 10% pooled human serum. Supernatant was removed after 24 hours, and TNF content was determined in an assay on WEHI cells, as described by Traversari et al., Immunogenetics 35: 145–152 (1992), the disclosure of which is incorporated by reference.

The results, set forth in FIG. 1 demonstrate that a tumor rejection antigen, derived from MAGE-1 is presented by HLA-Cw*1601, and is recognized by CTL clone 81/12, whereas expression of MAGE-2 and MAGE-3 does not lead to presentation of the appropriate antigen.

EXAMPLE 4

Following the experiments discussed supra, additional work was carried out to determine the peptide which HLA-Cw*1601 presented.

MAGE-1 cDNA in expression vector pcDNA I/Amp was digested with restriction endonucleases NotI and SphI following the supplier's instructions, and then with exonuclease III. This treatment generated a series of progressive deletions of the MAGE-1 cDNA, starting at the 3' end.

The deletion products were ligated back into pcDNAI/Amp, and then electroporated into E. coli strain DH5αF'IQ, using well known techniques. The transformants were selected with ampicillin (50 ug/ml), and six hundred clones were obtained.

The plasmid DNA was removed from each clone, and was then transfected into COS-7 cells, together with a vector which coded for HLA-Cw*1601. The protocol used follows the protocols described above.

The transfectants were then tested in the TNF release assay described in example 3. This permitted separation of positive and negative clones. The comparison showed that one of the positive clones contained nucleotides 1–730 from the MAGE-1 gene, while a negative clone contained nucleotides 1–706. The sequence of positive and negative clones was compared, and a region of 16 amino acids was identified as putatively containing the antigenic peptide. This sequence is:

Glu His Ser Ala Tyr Gly Glu Pro Arg Lys Leu Leu Thr Gln Asp Leu (SEQ ID NO: 2)

Based upon this sequence, a first set of experiments was carried out where synthetic peptides were made, and tested for their ability to render COS-7 cells transfected with HLA-Cw*1601 capable of stimulating lysis. A positive 12 mer was identified, i.e.:

Glu His Ser Ala Tyr Gly Glu Pro Arg Lys Leu Leu (SEQ ID NO: 3)

Truncation of this 12 mer led to the identification of nonapeptide

Ser Ala Tyr Gly Glu Pro Arg Lys Leu (SEQ ID NO: 4) as the best stimulator of lysis. Half maximal lysis was observed at a peptide concentrations of 10 nM.

In experiments not presented herein, but set forth in Ser. No. 08/196,630, filed Feb. 15, 1994 and incorporated by reference herein, the peptide Ala Ala Arg Ala Val Phe Leu Ala Leu (SEQ ID NO: 5) was also found to be presented by HLA-Cw*1601, and lysed by various cytolytic T cell clones, such as CTL 82/82.

EXAMPLE 5

The identification of two separate peptides being presented by HLA-Cw*1601 suggested the desirability of an assay to determine expression of HLA-Cw*1601 in patients. Serological testing is not a viable option because antibodies to HLA-Cw*1601 are not available. Polymerase chain reaction ("PCR"), however, provided an alternative. Development of a viable, useful PCR assay for expression of HLA-Cw*1601 based upon a nested primer system follows.

The model described generally by Browning et al., Proc. Natl. Acad. Sci. USA 90: 2842 (1993), was used. This reference discusses the use of oligonucleotide primers, the 3' ends of which are specific for the coding sequence for the HLA molecule. Using this approach, primers:

5'-CAAGCGCCAGGCACAGA-3' (SEQ ID NO: 6) and

5'-GCCTCATGGTCAGAGACGA-3'(SEQ ID NO: 7)

were synthesized. To test the method, various cell samples from patients were used. Total RNA was extracted, using the well known guanidine isothiocyanate method of Davis et al., *Basic Methods in Molecular Biology* (Elsevier, N.Y., 1986), pp. 130. For cDNA synthesis, 2 ug of RNA was diluted with water, and 4 ul of 5× reverse transcriptase buffer. Added were 1 ul each of 10 mM dNTP, 2 ul of a 20 uM solution of oligo (dT), 20 U of RNasin, 2 ul of 0.1M dithiothreitol, and 200 U of MoMLV reverse transcriptase, in a 20 ul reaction volume. The mixture was incubated for 60 minutes at 42° C. To amplify the cDNA, 1% of the cDNA reaction was supplemented with 5 ul of 10× thermostable DNA polymerase buffer, 1 ul each of 10 mM dNTP, 0.5 ul each of 80 uM solution of primers (SEQ ID NO: 6 and 7), 1U of DynaZyme, and water to a final volume of 50 ul. The PCR was carried out for 30 cycles (one minute at 95° C., one minute at 62° C., two minutes at 72° C.). The products were diluted to 1/500. Then, a second PCR was carried out, using 1 ul of diluted PCR product, supplemented with 5 ul of 10× thermostable DNA polymerase buffer, 1 ul each of 10 mM dNTP, 0.5 uM each of a 80 uM solution of primers:

5'-GAGTGAGCCTGCGGAAC-3' (SEQ ID NO: 8) and

5'-CCTCCAGGTAGGCTCTCT-3' (SEQ ID NO: 9), and 1U of DynaZyme. SEQ ID NO: 8 and SEQ ID NO: 9 represent nucleotide sequences located internally to the first set of primers, i.e., SEQ ID NOS: 6 and 7. Water was added to 50 ul, and 20 cycles of PCR were carried out (one minute 95° C.; one minute at 65° C.; two minutes at 72° C.). The PCR products were then size fractionated on a 1.5% agarose gel in TAE buffer.

This methodology was utilized in two separate sets of experiments. In the first of these, transfectants, prepared as described supra and lysed by cytolytic T cell clones against either SEQ ID NO: 4 or SEQ ID NO: 5 complexed to an HLA molecule were tested. All positive transfectants were found to present the HLA-Cw*1601 molecule on their surfaces. Any sample which generated no PCR products was considered negative. In further experiments using the negative samples, the PCR protocol utilized above was employed a second time but the primers were based upon sequences common to all HLA-C sequences. See Zemmour et al., J. Exp. Med. 176: 937 (1992), incorporated by reference herein. The negative samples proved to be cells expressing different, i.e., non HLA-Cw*1601 HLA-C subtypes.

EXAMPLE 6

In the second set of experiments, the ability of cells, either PBL or tumor, to present peptides via HLA-Cw*1601, was tested. To do this, cells taken from patients were washed in Hank's solution, and resuspended at $5 \times 10^6$ cells/ml. They were then fixed by treating them for 10 minutes, at room temperature, with 1% paraformaldehyde. Following fixation, they were washed, twice, in Hank's solution, and resuspended in Iscove's medium with 10% human serum added.

The cells were then distributed in 96V-bottom wells, at either $3 \times 10^4$ PBLs or $1 \times 10^4$ tumor cells, and pulsed with varying concentrations of peptides. After two hours of incubation at 37° C., the cells were washed, twice, before CTLs (1500, 100 ul Iscove medium, 10% human serum, 20 U/ml recombinant human IL-2) were added, and TNF release from WEHI-164 cells measured. See, e.g., Traversari et al., Immunogenetics 35: 145 (1992), incorporated by reference for particulars of the assay. The effector cells in the assay were from CTL 82/35.

The results are summarized in the following table. TNF was only produced in the presence of target cells, derived from patients who had tested positive for HLA-Cw*1601, based upon the PCR assay, set forth supra, which had been pulsed with peptide.

The experiments, summarized in Table 1, used cells which had been fixed with glutaraldehyde, pulsed with the peptide, and then tested for recognition by cytolytic T cell line CTL 82/35. As the table shows, TNF was produced only in the presence of peptide pulsed target cells, which had tested positive for HLA-Cw*1601 in the PCR assay discussed supra.

TABLE 1

| Patient | HLA-Cw*1601 PCR | Peptide Presentation To CTL 82/35 |
| --- | --- | --- |
| MZ2 | + | + |
| LB17 | + | + |
| LB678 | + | + |
| LB708 | + | + |
| MI4024/1 | + | + |
| LB73 | − | − |
| LY-2 | − | − |
| SK19 | − | − |
| SK37 | − | − |

EXAMPLE 7

Approximately 8% of samples (7 of 99) were positive for this HLA type, and five of the positives were tested for CTL lysis; as described supra. All provoked lysis, as indicated in Table 1. In contrast, samples from four patients who were not positive for HLA-Cw*1601, did not provoke lysis by CTLs.

EXAMPLE 8

In another experiment, MZ2 lymphoblastoid cells, infected with Epstein Barr Virus, were used in a $^{51}$Cr release assay. The infected cells, referred to as "MZ2-EBV", were $^{51}$Cr labelled, and then incubated for 30 minutes in the presence of MAGE-1 peptide, at concentrations ranging from 1 to 5000 nM. CTLs (either CTL 81/12 or CTL 82/35) were added at an effector/target ratio of 3:1. Chromium release was measured after four hours.

Figure 2B:
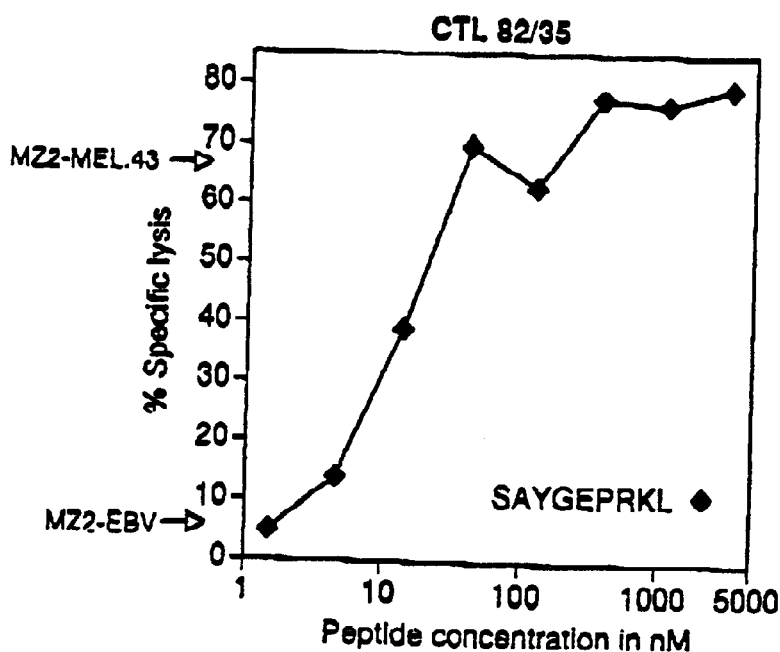
FIG. 2B parallels FIG. 2A, the only difference being that the effector was CTL 82/35.

The results are shown in FIGS. 2A and 2B, showing lysis by CTL 81/12 (FIG. 2A) and CTL 82/35 (FIG. 2B). Arrows indicate the level of lysis of MZ2-MEL 43(B$^+$) and MZ2 lymphoblastoid cells (B$^-$), incubated without peptides.

The experiments set forth supra suggest that a peptide with a particular binding motif is required for binding to HLA-Cw*1601. Peptides of this formula, i.e.:

Xaa Ala (Xaa)$_6$ Leu (SEQ ID NO: 10), are one feature of the invention. In SEQ ID NO: 10, Xaa refers to any amino acid, with the following preferences:

Ala or Ser at position 1
Tyr or Arg at position 3
Gly or Ala at position 4
Glu or Val at position 5
Pro or Phe at position 6
Arg or Leu at position 7
Lys or Ala at position 8

Isolated peptides of this formula are useful, e.g., in diagnosing cancer, as will be explained. It is known, as per the references cited herein, that patients do develop cytolytic T cells against their own tumors. For HLA-Cw*1601 positive patients, these cytolytic T cells recognize and react with any cell which presents complexes of HLA-Cw*1601 and a peptide of the formula in SEQ ID NO: 10, most preferably SEQ ID NO: 4 or SEQ ID NO: 5. The recognition may be monitored via TNF release by the CTLs, proliferation of the CTLs, and/or release of some agent contained by the target cells, e.g., radioactive chromium ($^5$Cr). Thus, in one aspect of the invention, a sample of a subject's blood, containing PBLS, is contacted to HLA-Cw*1601 presenting cells. These cells are contacted, such as by pulsing, with a peptide in accordance with SEQ ID NO: 10. These peptides complex with the HLA-Cw*1601 molecules, and any CTLs in the PBL containing sample react therewith. Thus, one aspect of the invention is a diagnostic assay for the determination of tumor specific CTLs, it having been established that only tumor cells present MAGE derived TRAs. The one exception to this appears to be testicular cells, but it is a simple matter to simply exclude the possibility that CTLs in the subject's blood are reacting with testes cells. One may also transfect an HLA-Cw*1601 positive cell with a MAGE gene, e.g., MAGE-1, to produce the desired complexes.

In another aspect of the invention, the peptides disclosed herein may be used alone or complexed to carrier proteins, and then be used as immunogens. Such immunogens can be used alone, or preferably with a pharmaceutically acceptable adjuvant. The antibodies are useful, also in diagnostic assays, to determine if and when the particular peptides are presented on cells. Again, such presentation is indicative of cancer.

The isolated nucleic acid molecules of the invention are also useful, as indicated, as probes for the determination of expression of HLA-Cw*1601. It hardly needs to be said that HLA typing is important in, e.g., tissue typing for transplantation, and other areas. Thus, it is useful to have available materials which can be used in this context. The primers used in the PCR work can be used, alone or in combination, in amplification assays such as polymerase chain reaction. They can also be used, when labelled, e.g., radioactively or non-radioactively, as probes for determining whether or not HLA-Cw*1601 is expressed, in other diagnostic assays. Thus, combinations of two or more of SEQ ID NOS: 6, 7, 8 and 9 may be used, in "one-pot" or kit forms, as diagnostic reagents. A kit form is expressly preferred, where separate portions of SEQ ID NOS: 6 and 7 and SEQ ID NOS: 8 and 9 are provided, in a packaging means, for use in an amplification or other formats. The kits may also include polymerases, such as Taq polymerase, in specific embodiments.

The foregoing experiments demonstrate that HLA-Cw*1601 presents a MAGE-1 derived peptide as a tumor rejection antigen, leading to lysis of the presenting cells. There are ramifications of this finding, discussed infra. For example, CTL clone 81/12 is representative of CTLs specific for the complex in question. Administration of such CTLs to a subject is expected to be therapeutically useful when the patient presents HLA-Cw*1601 phenotype on abnormal cells. It is within the skill of the artisan to develop the necessary CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. It has been pointed out that the sequence for HLA-Cw*1601 is known to the art through GENBANK and EMBL, and the sequence for MAGE-1, together with a detailed protocol for its isolation, is provided by the PCT application and Van den Bruggen et al., both of which are incorporated by reference in their entirety, supra. COS cells, such as those used herein are widely available, as are other suitable host cells.

To detail the therapeutic methodology, referred to as adoptive transfer (Greenberg, J. Immunol. 136(5): 1917 (1986); Riddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by abnormal cells presenting the particular complex. The CTLs then lyse the abnormal cells, thereby achieving the desired therapeutic goal.

The foregoing therapy assumes that the subject's abnormal cells present the HLA-Cw*1601/MAGE-1 derived peptide complex. This can be determined very easily. For example CTLs are identified using the transfectants discussed supra, and once isolated, can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression of MAGE-1 via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplify this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining MAGE-1 itself with an adjuvant to facilitate incorporation into HLA-Cw*1601 presenting cells. The enzyme is then processed to yield the peptide partner of the HLA molecule.

The foregoing discussion refers to "abnormal cells" and "cellular abnormalities". These terms are employed in their broadest interpretation, and refer to any situation where the cells in question exhibit at least one property which indicates that they differ from normal cells of their specific type. Examples of abnormal properties include morphological and biochemical changes, e.g. Cellular abnormalities include tumors, such as melanoma, autoimmune disorders, and so forth.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nonapeptide of formula

Xaa Ala Tyr Xaa Xaa Xaa Xaa Xaa Leu (SEQ ID NO: 11, 12, 13, 14, 15 or 16)

wherein Xaa in position 1 is Ser, Xaa in position 4 is Gly, Xaa in position 5 is Glu, Xaa in position 6 is Pro, Xaa in position 7 is Arg, or Xaa in position 8 is Lys.

2. An immunogenic composition comprising the isolated nonapeptide of claim 1, and a pharmaceutically acceptable adjuvant.

3. The immunogenic composition of claim 2, wherein said isolated nonapeptide is complexed to a carrier protein.

4. An isolated nonapeptide of formula

Xaa Ala Tyr Xaa Xaa Xaa Xaa Xaa Leu (SEQ ID NO: 17)

wherein Xaa is any amino acid.

* * * * *